United States Patent [19]
Williams et al.

[11] Patent Number: 5,547,680
[45] Date of Patent: Aug. 20, 1996

[54] METHOD FOR PREPARING A TOPICAL, AMINOCAPROIC ACID CONTAINING OPHTHALMIC GEL

[75] Inventors: Patricia B. Williams, Norfolk; Earl R. Crouch, Jr., Virginia Beach, both of Va.

[73] Assignees: Eastern Virginia Medical School, Norfolk; The Center for Innovative Technology, Herndon, both of Va.

[21] Appl. No.: 444,679

[22] Filed: May 19, 1995

Related U.S. Application Data

[62] Division of Ser. No. 390,788, Feb. 17, 1995, Pat. No. 5,505,954, which is a continuation of Ser. No. 223,837, Apr. 6, 1994, Pat. No. 5,415,863.

[51] Int. Cl.$^6$ .................................. A61K 31/195
[52] U.S. Cl. .............. 424/427; 424/428; 424/78.04; 514/561; 514/772; 514/912; 514/647; 514/944
[58] Field of Search .................................. 424/427, 428, 424/450, 78.04; 514/912–916, 673, 647, 561, 772, 944

[56] References Cited

U.S. PATENT DOCUMENTS 4,804,539  2/1989  Guo ........................................ 424/450

OTHER PUBLICATIONS

A Uingham et al Archives of Ophthalmology 105, 1987, p. 1421.

A Uingham et al Archives of Ophthalmology 106, 1988 p. 1436.

Ehlers et al Invest— Ophthalmology Vis Science 31, 1990 p. 2389.

*Primary Examiner*—Gollamudi S. Kishore
*Attorney, Agent, or Firm*—Whitham, Curtis, Whitham & McGinn

[57] ABSTRACT

A topical gel formulation containing aminocaproic acid prevents secondary hemorrhage following hyphema without the adverse side effects associated with systemically delivered aminocaproic acid. Of ten human patients treated with the formulation, none have experienced a secondary hemorrhage and none have experienced adverse side effects. The topical gel formulation is prepared by a process which ensures sterility, a pH compatible with conditions in the aqueous humor, and optimum consistency. A permeation enhancer such as proparacaine can be incorporated into the gel during formulation and be used to enhance the transport of aminocaproic acid across the corneal epithelium.

6 Claims, No Drawings

METHOD FOR PREPARING A TOPICAL, AMINOCAPROIC ACID CONTAINING OPHTHALMIC GEL

CROSS REFERENCE TO RELATED APPLICATION

This application is a divisional of U.S. patent application Ser. No. 08/390,788 filed Feb. 17, 1995, now U.S. Pat. No. 5,505,954 which is a continuation of U.S. patent application Ser. No. 08/223,837 filed Apr. 6, 1994, now U.S. Pat. No. 5,415,863.

BACKGROUND OF THE INVENTION

1. Field of the Invention

The present invention generally relates to a formulation used to decrease the incidence of secondary hemorrhage after hyphema and, more particularly, to a topical formulation which includes aminocaproic acid which is applied to a patient's eye.

2. Description of the Prior Art

Injuries caused by a blow to the eye are referred to as hyphema. These injuries include puncture wounds, such as would occur with a pencil or nail, as well as wounds resulting from the impact of a hard object, such as a baseball or racquetball. Secondary hemorrhage is a serious complication of traumatic hyphema where a rebleed at the injured site occurs. When a patient experiences a secondary hemorrhage, the rebleeding generally occurs within two to five days after the initial injury. Secondary hemorrhage is usually more severe than the initial hemorrhage and significantly worsens the prognosis of an already traumatized eye. Secondary hemorrhage occurs in 18% to 38% of traumatic hyphemas, and the overall incidence is approximately 25%. With secondary bleeding, the incidence of glaucoma increases to 50%, and there is a much greater chance of corneal blood staining and optic atrophy.

An oral form of $\epsilon$-Aminocaproic acid (ACA) developed in the mid-1970s has been shown to significantly reduce the incidence of secondary hemorrhage. ACA is an antifibrinolytic agent and functions by inhibiting plasminogen activity, thereby reducing the tame of enzymatic breakdown of a clot. The typical dosage of oral ACA ranges from 50 mg/kg per dose to 100 mg/kg per dose. A drawback of orally delivered ACA is that administration of the drug is required every four hours. More importantly, many adverse affects have been observed when ACA is provided orally or by other systemic routes (e.g., peritoneal or intravenous injection). Specifically, patients have been reported to experience nausea and vomiting, dizziness, systemic hypotension, and syncopal episodes. Vomiting is one of the worst side effects of orally administered ACA because vomiting puts pressure on the eye which may actually cause a secondary hemorrhage. Although decreasing the dose of aminocaproic acid (50 mg/kg per dose) appears to decrease the incidence of some of these adverse effects, many ophthalmologists are still reluctant to institute treatment with systemic ACA.

Loewy et al., *Arch. Ophthalmol.*, 105:272–276 (1987) reported studies of the plasma and aqueous humor pharmacodynamics of intravenously administered ACA. Peak aqueous humor ACA levels of 1.3 and 3.3 mg/dL were obtained after administration of 50- and 100-mg/kg intravenous boluses, respectively. When ACA was given by infusion at 25 mg/kg/h, the peak concentration was 0.25 mg/dL in the aqueous humor. Plasma concentrations ranged from 3.5 mg/dL (infusion, 25 mg/kg/h) to 25.5 mg/dL (100 mg/kg bolus). Antifibrinolytic activity was found to parallel ACA concentrations in both the plasma and the aqueous humor.

Allingham et al., *Archives of Ophthalmology*, 105:1421–1423 (1987), reported that polyvinyl alcohol and carboxypolymethylene, a carbomer gel and hydrophilic polymer referred to hereinafter as carbopol, are good vehicles for providing ACA to the aqueous humor by topical administration. Specifically, it was found that ACA dissolves in these vehicles, and that solutions of polyvinyl alcohol with 735 g/L of ACA and carbopol with 600 g/L of ACA which were topically applied to the eyes of test rabbits resulted in ACA levels in the aqueous humor comparable to those obtained by intravenous infusion (25 mg/kg/h). Most notably, the plasma levels in the rabbits treated with the topical ACA preparations were 5 to 33% of those observed in Loewy et al. with intravenous ACA administration. Hence, it was suggested that topically applied ACA could be developed to treat traumatic hyphema since suitable ACA levels could be achieved in the aqueous humor with reduced systemic side effects since systemic ACA levels with the topically applied ACA were significantly reduced.

Allingham et al., *Archives of Ophthalmology*, 106:1436–1438 (1988), reported that topically applied aminocaproic acid significantly reduces the incidence of secondary hemorrhage in traumatic hyphema in the rabbit model. In the study, rabbits with experimentally induced traumatic hyphemas were treated with topical placebo (4% carbopol gel only) and with carbopol gel containing ACA. In the control and placebo groups, there was a 33% rebleed rate, while in the treated eyes there was only a 10% rebleed rate which was statistically significant. No evidence of systemic toxicity was observed in the rabbits. In addition, in the study, droplets of 0.5% proparacaine were provided to the rabbit eyes prior to installation of the gels. Proparacaine is a local anesthetic that can increase corneal penetration of ACA.

Ehlers et al., *Ophthalmology & Visual Science.* 31:2389–2394 (1990), reported studies related to optimized topical ACA formulations and dosing schedules in the rabbit model. In the studies, the ACA concentration in the topical formulations was varied from 15% to 60% and the carbopol gel vehicle concentration was varied from 0.5% to 4%. In addition, the dose size, frequency of dosing, the effects of pretreatment with topical anesthetics, and the effect of simulated patching of the eye were examined. It was determined that the optimum topical regimen in the rabbit model was 200 µl of 30% ACA in 2% carbopol every six hours in unpatched eyes. The administration of proparacaine droplets prior to instilling the topical ACA containing gel was found to significantly enhance the penetration of ACA in the aqueous humor.

The above studies, all of which were conducted under the supervision of the joint-inventors of this patent application, Dr. Crouch and Dr. Williams, show that a topical formulation of aminocaproic acid would be superior to the orally delivered drug since the adverse systemic side effects would be avoided. Nevertheless, formulating a suitable topical ACA gel for clinical use on human beings poses considerable challenges. Achieving a pH in the gel where the pH throughout the gel is uniform is required for safety in topical ophthalmic products. In addition, suitable topical gels must have a solubility and consistency which allows spreading the ACA gel over the corneal epithelium without losing contact with the corneal epithelium. Furthermore, achieving sterility of the ophthalmic product is required, but difficult to achieve with a gel since filter sterilization and heat sterilization techniques cannot be used. Moreover, despite the fact that the earlier work was performed with rabbits, the earlier work does not disclose a product formulation suitable for use on animals by a veterinarian since the problems of pH, solubility and consistency, and sterility remain a concern.

SUMMARY OF THE INVENTION

It is therefore an object of this invention to provide a topical aminocaproic acid formulation which is suitable for clinical use on human beings and animals in reducing secondary hemorrhage arising from traumatic hyphema.

It is another object of this invention to provide a topical gel which includes both aminocaproic acid and proparacaine.

It is yet another object of this invention to provide a method of making a topical gel formulation which contains both aminocaproic acid and proparacaine.

According to the invention, topical gel formulations containing ACA dissolved in carbopol have been developed which are suitable for clinical use on human beings and animals. The topical gel formulations may ideally contain proparacaine as a local anesthetic. Formulation techniques have been developed to achieve proper pH, ACA solubility and gel consistency, and sterility.

DETAILED DESCRIPTION OF THE PREFERRED EMBODIMENTS OF THE INVENTION

As an example, a suitable ophthalmic gel formulation containing 30% ACA within the scope of this invention has the following ingredients: 30 grams ACA, 100 milligrams ethylenediamine tetraacetic acid (EDTA), 2 grams of carboxypolymethylene powder, and 100 ml of sterile water. ACA is available from Sigma Chemical Co., EDTA is available as a disodium salt from Aldrich Chemical Co., and carboxypolymethylene powder is available as carbopol 934P powder from BF Goodrich Co.

The ophthalmic gel formulation is prepared according to a procedure that ensures suitable pH conditions within the gel, optimum ACA solubility and gel consistency, and sterility in the resulting product. First, the carbopol powder is added to 25 ml of sterile waiter in an autoclavable container. Second, the pH of the carbopol/sterile water mixture is then adjusted to approximately 2.5 by titration with HCl. Other sterilized acid solutions may also be used for this purpose. Achieving a low pH in the preparation process at this point is needed since it will prevent the carbopol from forming a thick gel and makes both subsequent combining with ACA and sterilization of the gel easier. Third, the carbopol mixture is autoclaved to achieve sterility. Suitable autoclaving conditions include 250° F. for 30 minutes; however, the time and temperature for autoclaving can be varied significantly. The objective of autoclaving is to sterilize the carbopol gel vehicle. Other sterilizing techniques such as radiation exposure may be possible; however, filter sterilization is not possible with gel formulations. Fourth, the ACA and EDTA powders are dissolved in the remaining 75 ml of sterile water. Fifth, filter sterilize the ACA and EDTA solution into the sterile carbopol gel. This can be done with a final filter of 0.22 microns and serial filtration may be necessary. ACA cannot be heat sterilized since it both decomposes and discolors at the temperatures required for heat sterilization. Filter sterilization should be done in aseptically in a laminar air flow hood. Sixth, adjust the pH of the gel product to 7.4 by aseptically adding a sterile NaOH solution or other basic solution. The NaOH solution must contain 30% ACA to achieve a final product with 30% ACA. As above, the NaOH solution with ACA can be filter sterilized using a 0.22 micron filter. High performance liquid chromatography (HPLC) has been performed to confirm the 30% ACA final concentration. Seventh, prepare unit doses of the gel for administration to patients. A suitable unit dose could be prepared by adding 0.2 ml of the gel to each of several 1 ml Glaspak syringes where the syringes will be capped with a sterile tip. The shelf life of the topical ACA formulation is at least two years.

While the optimum gel formulation includes approximately 30% ACA and 2% carbopol, based on earlier test results with rabbits it is expected that the ACA concentration could range from approximately 10% to 60% by weight and the carbopol concentration could range from approximately 0.5% to 5% by weight. Gel formulations would be prepared as above; however, the concentrations of ACA and carbopol would be adjusted accordingly.

The function of EDTA in the solution is as a chelating agent. The concentration of EDTA optimally ranges between 0.05% and 0.25% by weight.

It has been determined that the ACA plasma levels in rabbits, after a systemic dose of ACA equivalent to the human oral dose on a mg/kg basis, correlate with the human plasma levels after the oral dose of ACA. In view of the earlier studies of the levels of ACA in plasma and aqueous humor, a target value of greater than 30 µg/ml ACA in the aqueous humor is believed to be optimum for human beings.

Proparacaine, a local anaesthetic which has been found to significantly enhance ACA penetration across the corneal epithelium, is ideally combined with the gel; rather, than being administered as drops prior to instilling the gel in a patient's eyes as has been described in the prior art investigations. In this way, a doctor is not required to undergo a two step process and is assured of having a sufficient amount of proparacaine present on the corneal epithelium. Administering drops of proparacaine prior to applying the gel can be time consuming and is inaccurate. Moreover, some ophthalmologists are reluctant to use proparacaine; hence, its presence in the gel will assure that the patient in fact receives the enhanced properties it provides to ACA.

The preparation of a gel with both ACA and proparacaine is according to the seven step process outlined above. The quantity of proparacaine should range between 0.5% and 30% by weight of the gel. Ideally, the proparacaine will be added to the filter sterilized NaOH solution containing an extra amount of ACA which, as discussed in the sixth stem of the formulation process, is added to adjust the pH of the gel product to pH 7.4. However, the proparacaine may also be added together with the ACA and EDTA to the sterile water as discussed in the fourth step of the formulation process. As an example of a 30% ACA gel with 0.5% proparacaine, a 25 ml gel sample would include 7.5 gms of ACA powder, 25 mg EDTA, 0.5 gms of carbopol 934P powder, 25 ml of sterile water (where 6.25 mls is initially combined with the carbopol and the remainder is combined with the EDTA and ACA), and 125 mg of proparacaine.

Rather than using proparacaine in the ACA containing gel, permeation enhancers such as BL-9, (polyoxyethylene 9-laurylether) Brij-78 (polyoxyethylene 20-stearylether) and saponin might be formulated into the gel. Since proparacaine physically disrupts the corneal epithelium, it may have some toxic side effects. The incorporation of less destructive permeation enhancers may provide for the enhanced ACA concentration in the aqueous humor without adverse side effects.

The gel formulation may be improved by incorporating ACA into liposomes such as those which may be created from soya lecithin, phosphatidyl choline, and other compounds. ACA is very water soluble and could be incorporated into lecithin liposomes. The size and shape of the lecithin liposomes could be adjusted by the addition of water. A particular advantage which is likely to arise from the incorporation of ACA in lecithin liposomes is that they may allow for a sustained release of ACA (e.g., ACA will be released topically over a longer period of time since the release of ACA will be a function of the time of breakdown for the lecithin liposomes). Increased concentrations of ACA might be used with the lecithin liposomes to prolong the usefulness of the gel.

In a comparison experiment with twenty one human patients having traumatic hyphema, ten patients were provided with a topical 30% ACA formulation prepared according to the seven step process described above and eleven patients were provided with the traditional systemic ACA formulation. The topical 30% ACA gel formulation was administered as 0.2 ml doses from a sterile Glaspak syringe onto the corneal epithelium of the eye every six hours. For the ten patients receiving the topical 30% ACA gel formulation, there have been no rebleeds observed and there have been no systemic side effects observed. In addition, no ocular side effects have occurred. For the eleven patients treated with the systemic ACA, there has been one secondary hemorrhage observed and one patient has experienced nausea and vomiting.

The formulation technique described above provides a number of advantages. First, the pH of the gel is adjusted to a level which is consistent with conditions in plasma and in the aqueous humor (e.g., pH 7.4). By adding NaOH, the acidity of ACA is overcome. By first adjusting the gel to an acidic and flowable form (e.g., adjusting carbopol solution to pH 2.5) and subsequently adding the basic (NaOH) solution, the formulation process assured that the basic solution (NaOH) would be evenly distributed in the gel, thereby achieving a uniform pH throughout the gel. Precautions were taken not to dilute the concentration of ACA in the gel by the addition of base. Second, the solubility and consistency of the gel formulated according to the seven step process has an optimum consistency. The solubility and consistency of the gel changes with the addition of ACA. The consistency of the gel is very important to an efficacious formulation since, with gels that are too thin, the product doe not remain in contact with the corneal epithelium, and, with gels that are too thick, the product does not spread over the corneal epithelium. With both gels that are too thick and gels chat are too thin, the ACA absorption into the aqueous humor decreases. Third, a sterilized product is produced in a two part process where the gel is heat sterilized and the ACA is filter sterilized. In this way, decomposition of ACA by heat sterilization is avoided. Moreover, the gel is sterilized by heat since filter sterilization of a gel is not possible.

Other vehicles and gels do not provide comparable results to the carbopol gels described above. For example, a gel of similar consistency which was prepared with ethylene maleic anhydride (EMA) and ACA was found to be toxic.

While the process of formulation has been shown to produce a gel which is effective for preventing secondary hemorrhage in human beings, the same techniques of pH adjustment and sterility assurance can be used to prepare topical gels used to treat animals.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A method for preparing a topical, aminocaproic acid containing ophthalmic gel, comprising the steps of:
   preparing a solution of carboxypolymethylene having an acidic pH;
   sterilizing said solution of carboxypolyethylene by heat sterilization;
   preparing an aminocaproic acid solution by combining aminocaproic acid with water;
   sterilizing said aminocaproic acid solution without decomposing or discoloring said aminocaproic acid by filter sterilization; and
   combining said solution of carboxypolymethylene and said aminocaproic acid solution after said heat and filter sterilizing steps to form a gel, wherein a concentration of said carboxypolymethylene ranges from 0.5% to 5% by weight of said gel, and said aminocaproic acid ranges from 10% to 60% by weight of said gel.

2. A method as recited in claim 1 wherein said step of preparing said aminocaproic acid solution further comprises combining ethylenediamine tetraacetic acid with said aminocaproic acid and said water.

3. A method as recited in claim 1 further comprising the step of adjusting the pH of said gel to approximately 7.4 by the addition of a base solution to said gel.

4. A method as recited in claim 3 further comprising the steps of adding aminocaproic acid to said base solution, and sterilizing said base solution containing said aminocaproic acid.

5. A method as recited in claim 4 further comprising the step of adding proparacaine to said base solution.

6. A method as recited in claim 1 further comprising the step of adding proparacaine to said gel.

\* \* \* \* \*